United States Patent [19]

D'Arnal

[11] 4,259,184

[45] Mar. 31, 1981

[54] SEALED CONTAINER ADAPTED FOR MEDICAL USAGE AND METHOD OF SEALING

[76] Inventor: Hubert A. D'Arnal, 350 N. Genesee Ave., Los Angeles, Calif. 90036

[21] Appl. No.: 956,356

[22] Filed: Oct. 31, 1978

Related U.S. Application Data

[63] Continuation of Ser. No. 718,576, Aug. 30, 1976, abandoned.

[51] Int. Cl.³ ...................... B01D 35/02; B01D 31/00
[52] U.S. Cl. ..................................... 210/85; 128/272; 141/329; 210/172; 210/464; 215/248; 215/313; 215/DIG. 3; 222/81
[58] Field of Search ................. 222/540, 512, 513, 80, 222/81, 249, 250, 476; 215/271, 270, 308, 309, 362, 364, DIG. 3, 320, 248, 313, 335; 55/279, 385 C; 210/450, 474, 475, 464, 469; 128/272

[56] References Cited

U.S. PATENT DOCUMENTS

| 2,191,447 | 2/1940 | Beardsley | 215/DIG. 3 |
| 3,905,368 | 9/1975 | Lewis, Jr. et al. | 128/272 |

FOREIGN PATENT DOCUMENTS

| 560517 | 9/1957 | Belgium | 215/DIG. 3 |
| 594234 | 11/1947 | United Kingdom | 128/272 |

*Primary Examiner*—Frank A. Spear, Jr.
*Attorney, Agent, or Firm*—Hill, Van Santen, Steadman, Chiara & Simpson

[57] ABSTRACT

A sealed container especially adapted for medical usage to receive and dispense fluids without contamination has a two orifice closure system whereby contaminants are kept out by a microfilter when an inlet orifice is opened for additions, and by a valve when an outlet orifice is opened for withdrawals. The closure has an upper removable seal and a lower fixed seal spaced from the upper removable seal and cooperating therewith in defining an operative space compartment sealed from both the interior of the container and the outside. In some embodiments, the lower seal has inlet and outlet passageways joining the interior of the container with the operative space compartment. An independent seal accessible from the operative space compartment is provided for the inlet passageway which is associated with the microfilter for stopping ingress of contaminants into the container. The valve provided at the outlet passageway is accessible from the operative space compartment to control outflow. The upper seal is removable to give access to the seal for the inlet passageway and the valve for the outlet passageway. The invention includes a method of preparing the container. The container holds liquids shielded from any contaminant, allows introduction of that liquid additive or air and allows withdrawl of the contents while avoiding at all times contact with any contaminants. The container may be evacuated to permit controlled vacuum induced introduction of liquid additives and air through the filter into the container.

27 Claims, 9 Drawing Figures

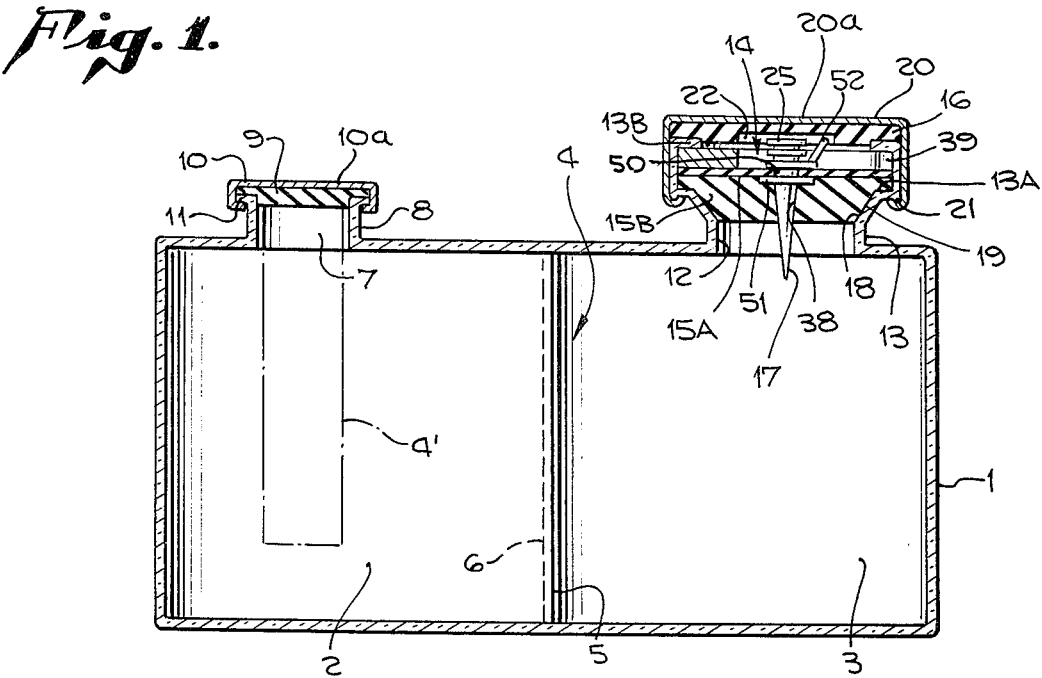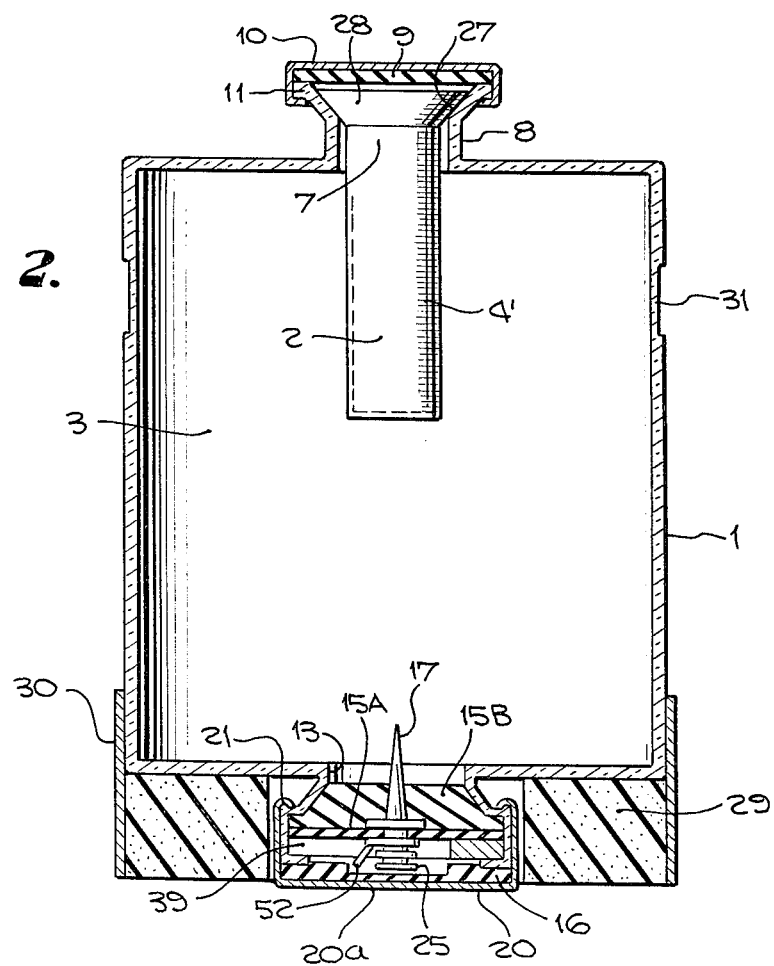

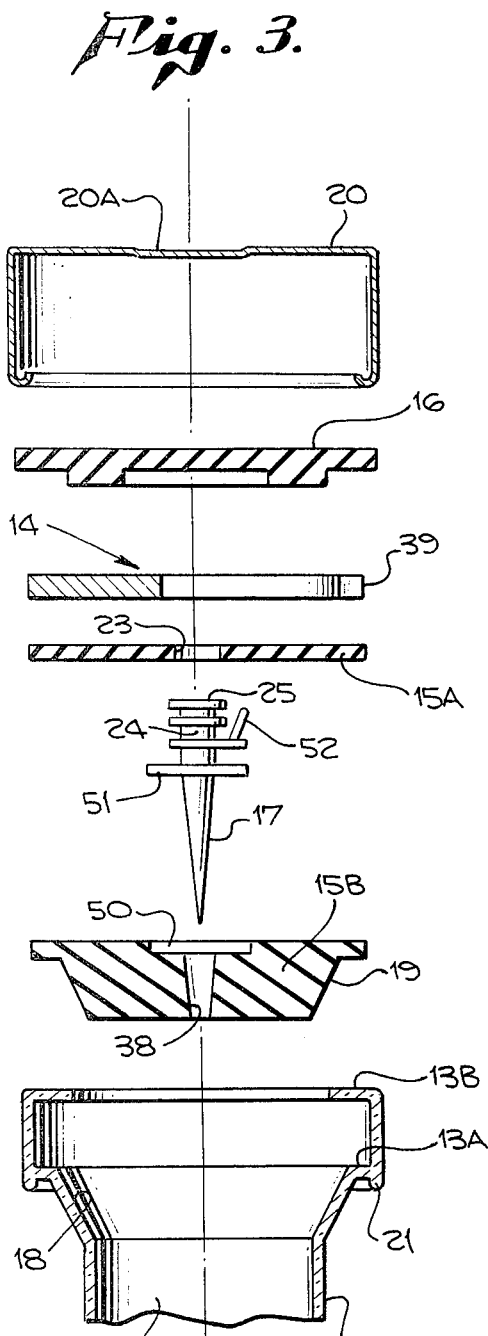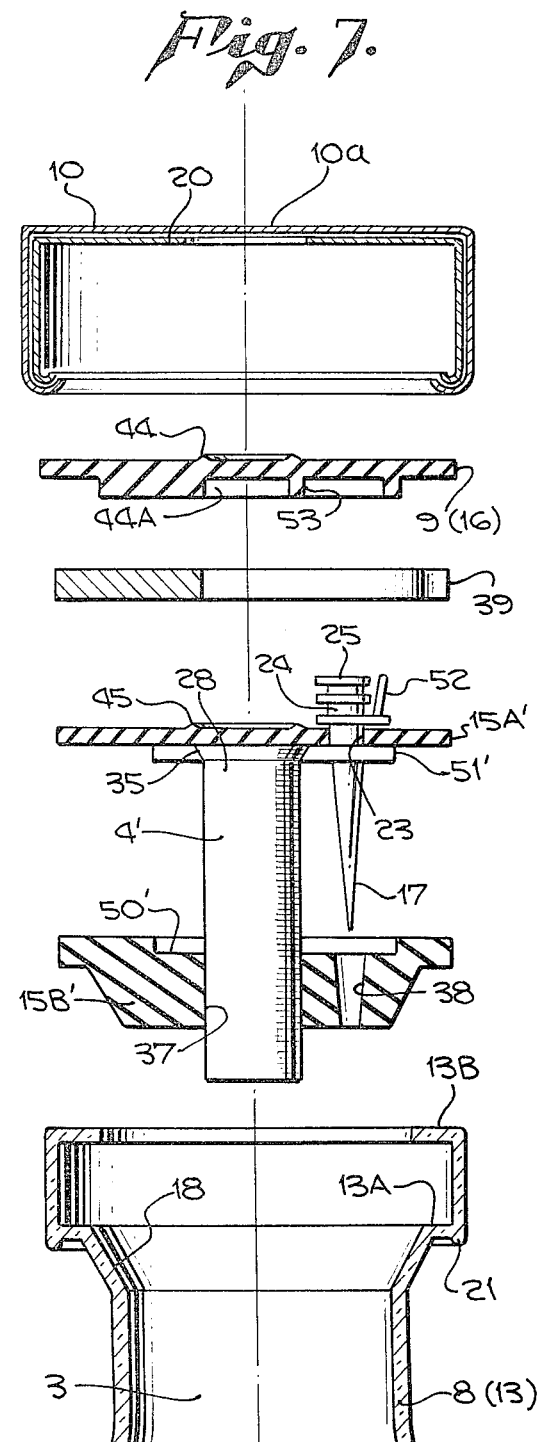

SEALED CONTAINER ADAPTED FOR MEDICAL USAGE AND METHOD OF SEALING

This is a continuation of application Ser. No. 718,576, filed Aug. 30, 1976, now abandoned.

BACKGROUND OF THE INVENTION

The invention deals with a hermetically sealed container, and aims primarily at the medical use of such container.

A first type of container currently in use includes a stopper, a membrane covering the stopper, and a cap crimped around the neck. The cap is precut so that a central portion may be removed uncovering a corresponding area of the membrane to which it gives access. The part of the cap that is left isolates hermetically the interior of the container with respect to the surrounding environment through the tight compression of the membrané over the stopper and through both against the neck. The stopper has two holes bored vertically in it. One is intended for the passage of the fluids to be withdrawn from the container, and the other is for the entry of the air that must replace those fluids.

Depending on the formulation, the contents may be placed inside the container either in an industrial plant for mass production, within a health care facility by completely extemporaneously compounding custom formulas, or by partial compounding by adding materials to the contents placed inside the container at the plant.

In the medical utilization of such containers in an ordinary environment, it is of critical importance in order to avoid detrimental effects on a patient's health such as septicemias and ischemias to avoid administering to the patients contents that have been contaminated by undesirable biologically active or inactive particles. Ischemias are caused by particles clogging smaller blood vessels, are particularly critical in certain organs and have been suspected by some to have some relation to certain forms of cancers.

At the industrial level, exacting procedures make it possible to end up with hermetically sealed containers free of any undesirable particle. This result is achieved thanks to sophisticated and expensive equipment handled by handpicked highly qualified professionals.

If a fluid is to be introduced into the container in a hospital setup, the operator pierces through the membrane with a hollow needle within a visual indicator or at the vertical of one of the holes mentioned, if existing in the stopper, and injects the fluid inside. This procedure involves the risk of contaminating the interior with undesired particles because the needle passing from the surrounding environment into the container may carry inside particles existing outside. Furthermore, the needle may also cut part of the membrane, the stopper or both, or it may allow the air outside to be sucked in because of the internal vacuum. Any germs reaching the fluids may proliferate even in the presence of preservatives.

For the administration of the container's contents to the patient, the membrane is broached at one of the two holes for the extraction of the fluids and at the other hole to permit the surrounding air to replace the departing fluid (replacement air). Some devices require one piercing only because they carry two canals on one stem; one canal allowing the fluids out and the other allowing the replacement air in.

A second type of container has only a single and smaller stopper without any hole bored in it nor any membrane on top of it. It is tightly compressed and kept in place by one or two crimped caps that are precut so that their central portion may be removed uncovering an equivalent area of the stopper. This stopper must again be pierced through its thickness for the extraction of its contents, either in a continuous manner (for slow perfusion), or repetitively in the course of time (vitamins, hormones, anibiotics), and to let in the replacement air. The larger containers usually are deprived of any internal gas when they leave the plant so that compounding is facilitated extemporaneously. However, air must be aspirated at the end of the compounding phase to eliminate the pressure differential before dispensing.

The containers of the second type are plagued by the same risks of contamination. With these two types of containers now in general use, any tampering with the original seals that is not very carefully monitored by a professional may cause at least a deformation of the elastic membranes letting in the surrounding air that may carry contaminants and suppress the pressure differential so helpful to compounding. As a matter of fact, this vacuum is necessary because it permits the insertion of additives without having to withdraw an equal volume of gas from inside. Furthermore, the presence of a vacuum at compounding or dispensing time after a long storage period is a very important safety check of air seepage and contamination.

To remedy these difficulties of extemporaneous utilization, one proposed measure is to include a rudimentary filter on the air inlet within the two-canal device mentioned earlier. However, this filter, which is close to the end to be inserted in the stopper, is regularly contaminated by the operator. It is common practice at the end of compounding to microfilter the full contents (post compounding microfiltration), particularly warranted in the case of large volume of fluids for parenteral fluid thereapy, or total parenteral nutrition, from which preservatives are barred.

In-line microfiltration is a common practice during dispensing of the fluids to the patient. These important microfiltrations are slow, tedious and leakprone, and they necessitate highly paid professionals using very expensive equipment.

The invention aims primarily at correcting these perplexing inconveniences and difficulties by providing a compact portable container with integrated shielding and operating features so that operations are rigidly limited and foolproof, resulting in continuously shielding the contents during the diverse manipulations.

Another object of the invention is to suppress the need for recreating very special environments at the time of utilization. The plant quality cannot be achieved without huge investments in equipment and professionals permanently on the alert.

SUMMARY OF THE INVENTION

To this end the container envisioned in the invention is characterized by the fact that it is arranged into an envelope housing a first and a second internal compartments, sepated one from the other by filtering means. A first and a second passageway enables each compartment to communicate respectively and separately with the surrounding environment (exterior). A first set of obturating means appropriate for the hermetical sealing of the first passageway is disposed in such manner as to permit the introduction of fluids from the exterior into the first compartment. A second and dual set of obturating means appropriate for the hermetical sealing of the second passageway comprises seal means and a stopper above the seal means. A communication tube transverses seal means from the interior of the second compartment to the operative space between the seal means and the stopper. The stopper is removable so that it permits access to the tube from the exterior to extract the contents of the second compartment by means of the tube.

In accordance with a preferred embodiment of this invention, the container has a single neck in or over which is disposed an elastic disc (part of the seal means) ensuring hermetic closure of the neck through contact and compression against the neck. The neck supports a filtering device, and the neck is traversed by the tube. The tube also passes through a sealing membrane (part of the seal means) in the neck. The stopper, which hermetically seals the upper end of the neck, is arranged so that it may be pierced simultaneously with the membrane for the introduction of fluids into the filtering device. The filter may be removed to permit proper access to the tube.

In accordance with this mode of embodiment preferred in the invention, the single neck is made into the proper configuration itself or through a cap or a sleeve, resulting in an operative space between two ledges on interior and inferior and the other superior and hanging over the interior. The interior ledge supports the elastic disc supporting the tube and the filtering device, and the exterior ledge supports and crimps the stopper. The space and arrangement between the two ledges being such that the membrane is compressed over the disc may be vigorously pressed against the lower ledge by a slotted ring elastically lodged under the lower face of the superior ledge in the operative space.

Other characteristics of the invention will appear while reading the following description which is given only as an example and made with reference to the drawings enclosed herein.

BRIEF DESCRIPTION OF THE DRAWINGS

FIG. 1 is a vertical section showing one embodiment of the container according to the invention;

FIG. 2 is a vertical section showing another embodiment of the container according to the invention;

FIG. 3 is an exploded view of one portion of the container shown in FIGS. 1 and 2;

FIG. 7 is an exploded view of a portion of the container shown in FIG. 4;

DETAILED DESCRIPTION OF THE PREFERRED EMBODIMENTS

Figure 4:
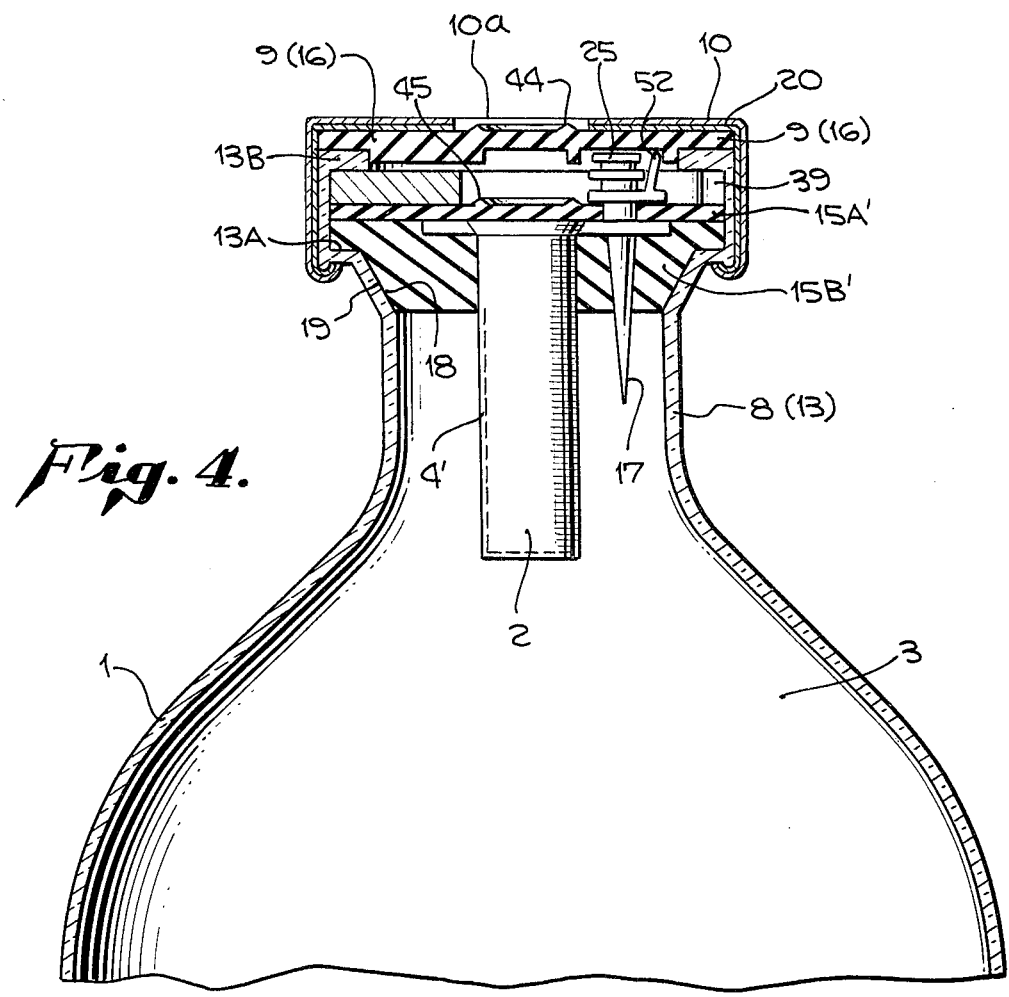
FIG. 4 is a vertical section showing a portion of the container according to another embodiment of the invention.

The container made according to the invention is intended so that it may hold liquid in its interior shielded from any undesired contaminant, allows the introduction extemporaneously of that liquid or of additives, and allows withdrawal of the contents while avoiding at all times contact with contaminants. Such container may serve in particular for the treatment of patients to whom the contents are dispensed in the form of a slow perfusion, but it may also serve for repeated small withdrawals made at sensible time intervals.

FIGS. 1 and 3 show one embodiment of the container according to the invention. The container has an envelope 1 made of glass, plastic, metal or otherwise. The internal space defined by envelope 1 is divided into two compartments 2 and 3 which are separated one from the other by a filtering wall 4, which can be shown as 4 (or 4') and arranged so that it allows the passage from compartment 2 into compartment 3 of fluids with or without particles having a diameter below a predetermined size. Particles used in the case of perfusions could be about 0.22 to 1 micron. Filter 4 could be made of a rigid porous material supporting lining 6 of filter material in compartment 2. Compartment 2 may communicate with the surrounding environment by a passageway 7, defined by a neck or opening 8 of the container. Stopper 9, which may for example be an elastic membrane, seals the container and is held in place by a cap 10 crimped around lip 11 on the external side of neck 8.

Compartment 3 may also communicate with the surrounding environment by a passageway 12, defined by a second neck or opening 13 of the container. As shown particularly in FIG. 3, neck 13 comprises an internal annular ledge 13A, and at its upper end it comprises an external annular ledge 13B, between which is defined an operative space 22. This neck is tightly sealed by the set of obturating means 14 which comprises an internal dual element 15 (15A and 15B), an external element of obturation 16, a hollow tube (canal) 17 and a slotted ring 39. (FIG. 3)

Element 15B is located below element 15A, and is a cylindro-conical disc made from compressible impervious material. Its cylindrical surface seats exactly on ledge 13A, and its conical portion 19 seats exactly on the corresponding surface 18. These corresponding dual cylindro-conical surfaces exist both on neck 13 and disc 15B so that the disc may hold in its place through friction and compression to seal the neck. The upper face of disc 15B has a central depression 50 that is intended to support annular expansion collar 51 of tube 17 for supporting the tube. Disc 15B has a central hole 39 at the center of cavity 50 for the passage of the lower portion of tube 17 shown below lip 51. Tube 17 could be modified for the specific uses of the container. It could extend to the bottom of the container and need not be tapered at its bottom as shown.

Thin flat disc or membrane 15A is made from a compressible and impervious material. It covers the upper face of disc 15B, and tube 17 is inserted into hole 23 by deforming disc 15B around the body of tube 17 above lip 51. Thus tube 17 is solidly and hermetically loaded and held between the dual elements 15 A & B. (FIG. 3)

Tube 17 which is preferably of plastic includes a valve 52 which may also be referred to as a tap or a faucet. Valve 52 may be actuated by a handle or otherwise from its upper end. Tube 17 has an outward widening mouth 24 (conical) that can be hermetically sealed by an appropriately shaped stopper 25. Tube 17, therefore, communicates between the interior of compartment 3 and the operational space 22 above disc 15A.

The set constituted by both discs 15A and 15B and tube 17 is held against neck 13 by slotted ring 39. (FIGS. 3 and 6) Ring 39 is vertically compressed and elastically deforms laterally within space 22 fitting exactly above membrane 15A and below the internal overhang of ledge 13B.

Ring 39 has two protrusions 40 and 41 (FIG. 6) having a holding means such as holes 42 on each extremity. To insert ring 39 the operator clamps holes 42 with an implement and presses protrusions 40 and 41 together to reduce the overall diameter of ring 39. After insertion, the protrusions can be released and the resiliency of ring 39 is urged against the wall of neck 13 below the lower face of ledge 13B. Ring 39 is pushing strongly downward aginst membrane 15A which pushes downward against disc 15B compressing both against inferior ledge 13A, thus constituting an internal seal of neck 13.isolating the interior of compartment 3 from that of operational space 22.

Thick stopper 16 has no holes. It seats on the upper face of ledge 13B and extends partially inside the central opening formed by ledge 13B. It is held tightly in place by a cap 20 (FIGS. 1 and 6) crimped around lip 21 of neck 13. This cap may be completely removed by tearing along precut lines starting with a flap 20A. When in place with cap 20 crimped on, stopper 16 hermetically seals the external mouth of neck 13 and thus isolates space 22, tube 17 and tube upper end 24 from the surrounding environment. If stopper 16 is removed, controlled access to these elements is possible.

The preparation and utilization of containers shown in FIGS. 1 and 3 are done as follows. The original mounting is done at the plant and contents may or may not be placed inside. Partial or complete filling may be done either at the plant or in a health care facility, extemporaneously in the latter case. Because of the controlled environment at a plant, necks 8 and 13 may be left entirely open and the contents placed directly through neck 13. Some obturating elements may be mounted forcing the access to compartment 3 through the canal of tube 17 whose valve 52 is the open position during the filling. Stoppers 25 and 16 would be removed. After filling and before sterilizing, the air inside must be removed. Neck 8 is hermetically sealed by tightly placing crimping cap 10 over lip 11 to secure member 9. Membranes 15A and 15B and tube 17 are placed in neck 13, and the slotted ring 39 holds the three of them in position to hermetically seal neck 13. Valve 52 is opened and both stoppers 25 and 16 are removed. Thus compartment 3 communicates with the surrounding environment by the canal of tube 17. Stopper 25 rests lightly in seat 24 on the upper end of tube 17, and stopper 16 lies on ledge 13B. The container is placed inside an autoclave, and the vacuum is increased. The air inside the container very slightly lifts both stoppers to escape from compartment 3 and space 22 until the desired vacuum is achieved and no air remains. Then both stoppers fall back into place, and sterile steam under pressure is admitted around the container. Under the maximum pressure differential both stoppers are forced in place sealing the container. Stopper 16 could be provided with means to close valve 52 when stopper 16 is forced into place. If not, stopper 16 would be removed so that valve 52 could be locked manually. Then vacuum processing would be repeated followed by sterilization and crimping.

For extemporaneous compounding within a health care facility, the precut central flap 10a of cap 10 on neck 8 is removed exposing the appropriate portion of stopper 9 where piercing should be done. This is done with a classical hypodermic hollow needle mounted on a syringe or tubing connected to the fluid to be injected. Enough air is injected to eliminate any remaining vacuum to avoid aspiration. It is possible in this manner to adjust the formulation of a container prepared in a plant to the specific needs of the patient. It is equally possible to start from an empty container prepared in the plant, and compound the entire formula extemporaneously within a health care facility.

Neck 13 is used to withdraw liquids to be administered. Precut flap 20A is removed so that cap 20 can also be removed. Stopper 16 is removed giving access to operative space 22 exposing the upper end 24 of tube 17 with its stopper 25 and valve 52 locked tightly so that compartment 3 is hermetically isolated. Stopper 25 is removed and replaced with a correspondingly shaped male tip which is connected to a hypodermic needle through plastic tubing. The air that must be admitted simultaneously with the outflowing of fuids is filtered and admitted through neck 8 through a needle inserted in stopper 9.

It is clear from the preceding that passageway 7 of neck 8 serves only for the introduction of liquids, solids dissolved in liquids, and air into compartment 2, and that passageway 12 serves only for the extraction of the contents of compartment 3. Compartment 3 throughout all manipulations is shielded from any contamination. As a matter of fact filter 4 retains any undesired particle that may have gotten into compartment 2 during the various piercings or that may be carried along by the air sucked in. Nothing enters through tube 17, not even air, because there is no vacuum.

With such a container, one is assured that the patient is administered a liquid free of any harmful particle. Another advantage of the invention is that it reduces manipulations to simple operations that can be harmlessly performed by an expanded body of health personnel. Another advantage of such container is that it puts high volume fluid therapy within reach of the most modest health facility with an excellent safety margin. Another advantage of the invention is that with this container one can do away with the two external microfiltrations described earlier. Another advantage of such container is that it prolongs very substantially the period of effective utilization of a drug whose container's seal has been broken for the purpose of making small infrequent withdrawals because of the effective isolation of the contents inside compartment 3 from contaminants. Another advantage of the invention is that it permits a longer preservation because of multistage obturating means that prevent air seepage much better.

FIG. 1 shows in phantom one variation in which the filter becomes miniaturized into a filter cartridge 4' that is attached to neck 8. This allows compartment 2 to become a tiny fraction of the size of compartment 3. (FIG. 2)

With reference to FIG. 2 and FIGS. 4 to 9, various other types of embodiments of the container are shown in accordance with the invention. Identical or analogous features may have identical reference numerals or they may have the same numeral added to 100 or 200.

In the embodiment shown in FIG. 2, necks 8 and 13 of envelope 1 are aligned on the opposing ends of the container. Filter 4' which separates compartments 2 and 3 is of the cartridge type. It attaches to neck 8 by its conical mouth 28 which is lodged in a corresponding conical surface 27 of neck 8. The latter is sealed by membrane 9 over which cap 10 is crimped around lip 11. A removable sleeve or drum 29 may cover the end on the side of neck 13 to protect it during the compounding phase. The cover thus achieved is held by friction against extension 30. The envelope has a conventional identation 31 near neck 8 for a holding strap (not shown) that permits hanging the container upside down for gravity flow to the patient.

The manufacture and the extemporaneous utilization of the container shown in FIG. 2 are similar to those described for containers shown in FIGS. 1 and 3 except that the container must be rotated 180° for use.

Both necks of the container may be formed on a lid that fits over a body. The lid of this drum-like container hermetically seals the drum and is secured by various means like screws.

The container shown in FIGS. 4 and 7 differs from those above in that it has only a single neck 8(13) which makes it very similar to the containers currently in use. Some features that in FIGS. 1 through 3 were associated respectively to necks 8 and 13 are common in FIGS. 4 and 7. Therefore, such features will be referred to by both numerical notations they had in FIGS. 1-3, e.g. neck 8(13).

Neck 8(13) has a conical surface 18 corresponding to surface 19 of the conico-cylindrical disc 15B'. Cartridge filter 4' is fitted through passage 37 bored through disc 15B' where it may be affixed for example by its widening out mouth 28. Disc 15B' also has a second hole 38 for the passage of the communication tube 17 whose circular lip 51' fits into cavity 50' in the upper face of disc 15B'. Note the increased size of lip 51' from lip 51 of FIGS. 1-3. Membrane 15A', a hermetical seal to cartridge filter 4, is above disc 15B' and covers open mouth 28. Membrane 15A' has a visual indicator 45 in relief on its upper face to locate the piercing locus.

Membrane 15A' is mounted within neck 8(13) with or without play and has a hole 23 so that it may elastically be slipped around the body of tube 17. Lip 51' also includes aperture 35 for supporting filter 4'. As in previous embodiments, tube 17 ends just above membrane 15A' and has the same mouth 24 widening out and sealed by stopper 25 and valve 52. Cartridge 4' is maintained tightly between membranes 15A' and 15B'. Slotted ring 39 pushing upwards against the lower face of ledge 13B pushes membrane 15A' downward against membrane 15B' and against ledge 13A sealing neck 8(13).

The upper end of neck 8(13) is hermetically sealed by a stopper 9(16) held tightly in place by two mating caps 10 and 20 both crimped around lip 11(21). On its upper face stopper 9(16) has a visual indicator 44 in relief for proper piercing. Within the boundaries of indicator 44, stopper 9(16) presents a cavity 44A on its opposite face to make stopper 9(16) thinner. Stopper 9(16) has another cavity 53 located above the upper end of tube 17. The top of cavity 53 presses stopper 25 and closes valve 52 when stopper 9(16) is tightly in place.

Figure 5:
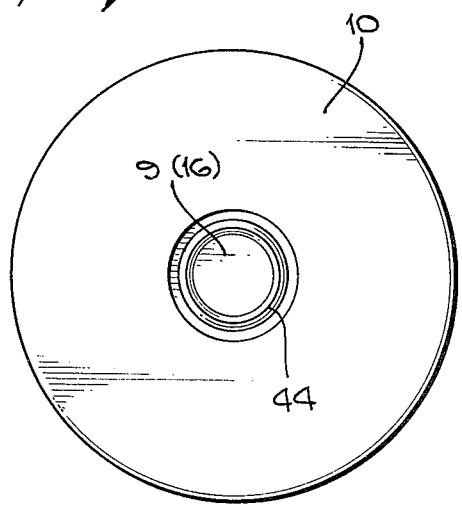
FIGS. 5 and 6 are plan views of the container of FIG. 4 showing what the operator sees during two phases of its utilization extemporaneously.

FIG. 5 is the operator's view of a factory-sealed container shown in FIG. 4 when central flap 10a of cap 10 has been peeled away. Cap 10 remains as an annular ring with a central window open and shows a portion of stopper 9(16) with its visual indicator 44 for proper injection. For the introduction of additives including air, a hollow needle connected to a syringe or appropriately to another container is inserted within indicator 44. Both stopper 9(16) and membrane 15A' are pierced simultaneously, and the needle is directed into filtering cartridge 4 by indicator 44.

Figure 6:
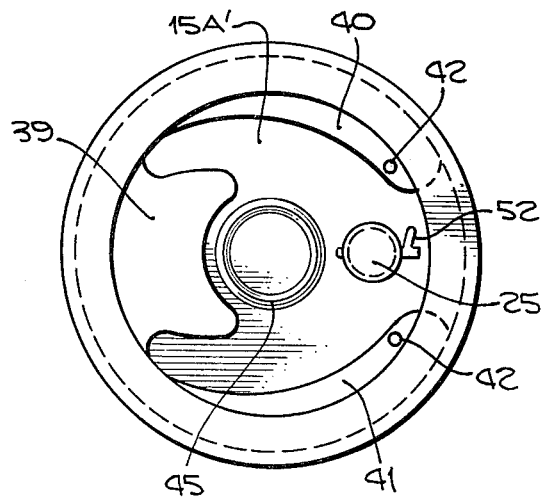

FIG. 6 is the operator's view of the container shown in FIG. 4 during the dispensing phase after the rest of cap 10, all cap 20 and stopper 9(16) are removed giving access to operative space 22. Membrane 15A', slotted ring 39 and the upper end of tube 17 with its stopper 25 and its valve 52, both placed in sealed position are visible. Stopper 25 may be safely removed and replaced by an equivalently shaped male tip for the extraction of the contents inside compartment 3 in the manner previously described. The tip may be connected to a hypodermic needle through plastic dispensing tubing. The needle is inserted into a patient's vein and valve 52 is opened allowing gravity flow of the fluids. A needle is inserted through membrane 15A' at indicator 45 to allow replacement air to enter through filter 4'.

Both caps 10 and 20 may have a precut removable central flap, but in the preferred embodiment internal cap 20 has an open window therethrough.

With such a container as shown in FIGS. 4 to 7, one is again assured that compartment 3 remains strictly shielded from any undesired particle throughout all extemporaneous manipulations. Any debris created by the needle during the piercing of stopper 9(16) (compounding phase) could be retained by membrane 15A', and any debris carved during the piercing of membrane 15A' (compounding and/or dispensing phase) and entering compartment 2 will be retained by filter device 4'. Any particles of the surrounding environment that may penetrate with a needle or with aspirated air will also remain in the filter. Finally no material enters compartment 3 by the channel of tube 17, because of the different seals, stopper 25, valve 52, and the previous suppression of any residual vacuum.

The container shown in FIGS. 4 to 7 may be made in the plant without any contents for extemporaneous compounding only. In the case of total parenteral therapy formulas, the double seals constituted by stopper 9(16) held by crimped caps 10 and 20 externally, and the dual element internally (15A, 15B), guaranty against air seepage over long storage periods. To inject liquids inside, one may remove caps 10 and 20 and then stopper 9(16), thus uncovering the upper end of tube 17 sealed by stopper 25 and valve 52. Membrane 15A' is pierced. Flap 10a only could be removed and both seals 9(16) and 15A' pierced.

Filtering cartridge 4' shown in FIGS. 4 to 7 could be modified by having the cartridge body fused in a one piece device to lip 51. Cartridge 4' could be replaced by a multiple canal passageway. Each canal would lead to a miniaturized nut-type filter of various mesh size. Visual indicator 45 of membrane 15A' would be marked so that each specific canal can be selected unambiguously. In this case the stopper 9(16) would be pierced simultaneously as described earlier, but would be removed before compounding.

Figure 8:
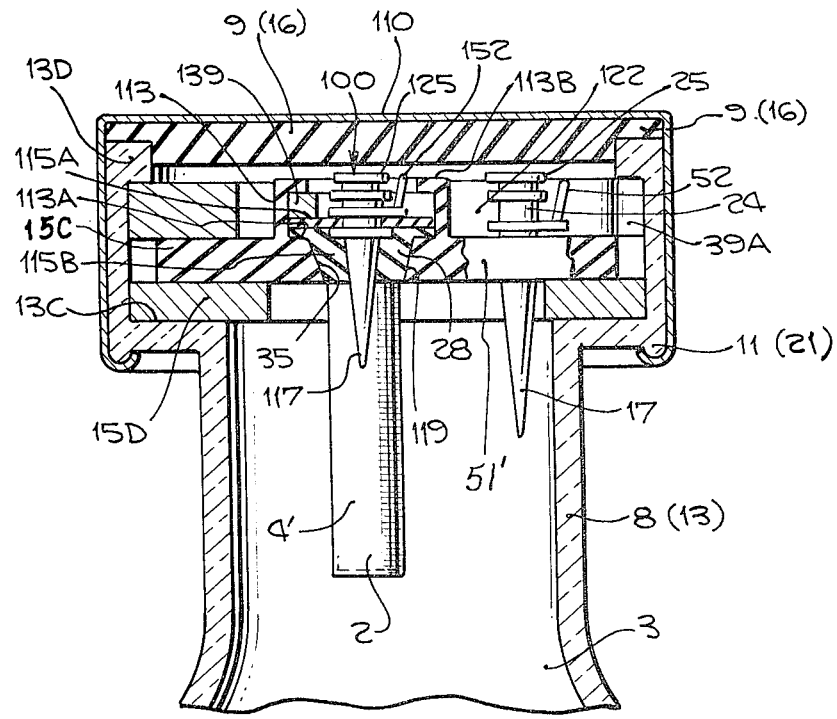
FIG. 8 is a vertical section showing a portion of a container arranged according to another embodiment of the invention.
Figure 9:
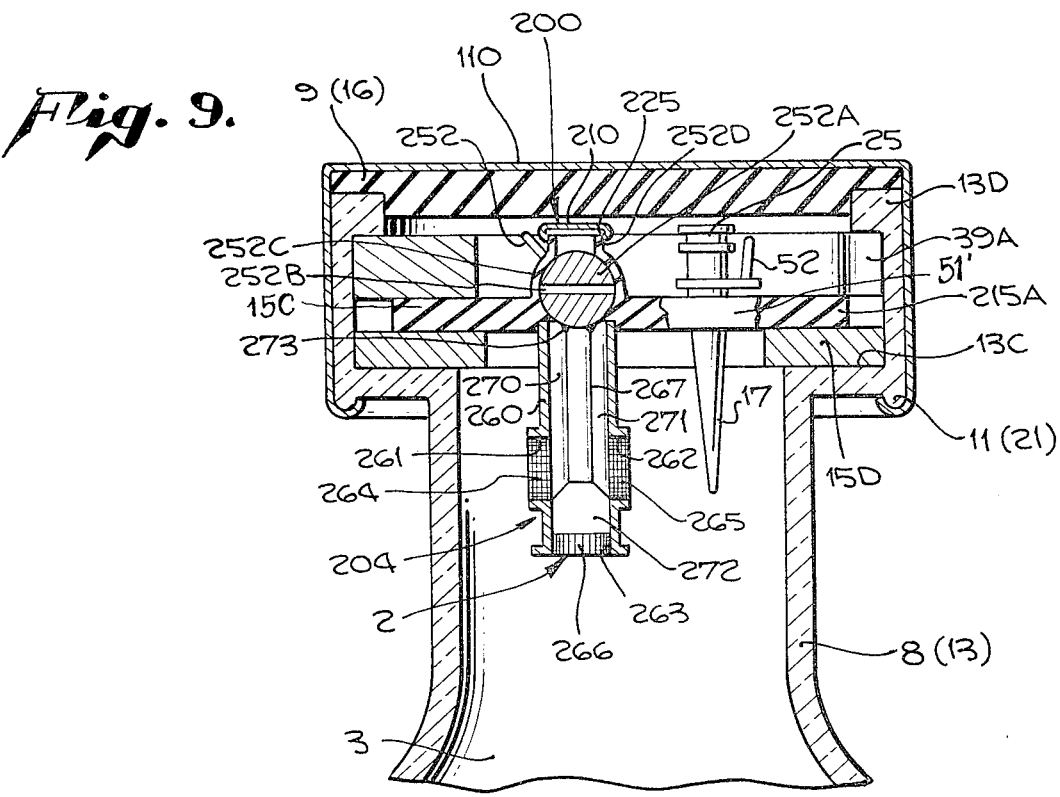
FIG. 9 shows a vertical section of another variation of a container according to the invention.

FIGS. 8 and 9 show two variations in which the introduction of liquids itself during formulation compounding does not require piercing of membrane 15A for access to compartment 2.

A portion of a container having a single neck similar to neck 13 shown in FIGS. 1 and 3 is shown in FIG. 8. This neck has both ledges 13C and 13D outlining operative space 122, and the lip 11(21) extends below ledge 13C. The elastic disc 15D is not conical. Rather, it is a flat annular ring or washer that seats on the similarly annular ledge 13C. Disc 15C which could be of compressible nature seats on disc 15D. Tube 17 is similar to that discussed before. Slotted ring 39A tightly presses downward on ledge 13C over annular disc 15D. Lip 51' could be formed as an integral part of disc 15C. In the exemplary embodiment of FIG. 8, the disc is replaced by an integral mounting to disc 15C which rests on disc 15D.

Disc 15C with a second opening 35 that supports means 100 for access to the container is organized as follows. Opening 35 is generally centrally located in the neck and tapers in a conical surface that cooperates with the widening mouth 28 of filtering cartridge 4'. Disc 115B seats by its conical portion 119 in mouth 28. Disc 115B is similar to the cylindroconical disc 15B in FIGS. 1 to 7. The obturating elements here, cylindroconical disc 115B, membrane 115A, tube 117, its valve 152, stopper 125 and the slotted ring 139 are analogous to the complex 15B, 15A, tube 17 and ring 39 shown in FIGS. 1 to 3.

Neck 113, similar in shape to neck 13 of FIG. 3, extends upward from disc 15C above opening 35. Neck 113 has an operative space between two ledges 113A inferior and 113B superior that function similarly to the parts associated with neck 13.

The upper ends of tubes 17 and 117 lay within operative space 122 above disc 15A and disc 15C. While neck 113 has no stopper of its own, neck 8(13) has a stopper 9(16) that seals it and space 22. Stopper 9(16) seats on and inside upper ledge 13D hermetically pressed and so kept by the crimping of cap 110 around neck 8(13) and its external lip 11(21).

For access to compartments 2 and/or 3, cap 110 and stopper 9(16) are removed, operative space 122 exposed showing both tubes 17 and 117, their valves 52 and 152, and stoppers 25 and 125 that allow controlled access to the corresponding compartments 2 and/or 3.

FIG. 9 shows a variation that differs from FIG. 8 by the organization of the filtering device, cartridge 204, and by the means of access to it. Neck 8(13), annular disc 15D, tube 17, slotted ring 39A and stopper 9(16) are identical to those shown correspondingly in FIG. 8.

Disc 215A which has been expanded into and fused with tube 17 and what had been disc 51 in the FIG. 7 embodiment, has two passageways or openings. The first for the access to compartment 3 is the canal of tube 17, the other opening leading inside compartment 2 through tube 200 which permits selection of microfilters. Tube 200 has a body 260 extending below disc 215A. Stopper 225 similar to stopper 25 of tube 17 is at the top of body 260 and below stopper 225 is a valve 252. A removable cap 200 may be crimped over neck 252D to hold stopper 225 in place.

Selection of the microfilter in the exemplary embodiment is as follows. Tube 260 may have three receptacles 261, 262 and 263 below disc 215A on which are fitted minisized filters 264, 265, 266 of mesh going from 0.22 to 1 micron, for example. A coaxial cylinder 267 inside tube 260 to whose internal wall it is linked lengthwise by two flanges, delimitates canals 270, 271 and 272 that each lead to a receptacle 261, 262 and 263.

Valve 252 which includes a rotating cylinder 252A that has a canal 252B directs fluid to one of the canals 270, 271, 272. Cylinder 252A is hermetically lodged inside a corresponding cylindrical cavity of the bulge 252C of tube 260. This bulge follows upward to form a neck 252D of tube 260 similar to the end 24 of tube 17. Valve 252 is maneuverable inside operative space 122 to open or close passageway 200 leading though its lower canal 260 inside the container. For example, cylinder 252A may be rotated to one of four positions. In the closed position, both openings of canal 252B are hermetically in contact with the solid wall of bulge 252C. In the three active positions, canal 252B is placed in line with the mouth of neck 252D on one hand and one of the canals 270, 271, 272. The separating cylinder 267 inside tube 260 carries hermetical seal 273 for isolating unused canals from canal 252B on valve 252.

For the utilization of FIG. 9, external cap 10(20) and stopper 9(16) are removed uncovering the upper ends of both tubes 17, 260. Valves 52 and 252 lock the passageway through both tubes. Stoppers 225 (with or without cap 210) and 25 are in the tubes. Valve 252 is in the locked position. Stopper 225 and cap 210 are removed. Communication is established between the fluid to be injected and the interior of the container through an appropriate male tip hermetically fitted into the mouth of neck 252D, and valve 252 is put in an active position that allows fluid flow to the preselected microfilter. The vacuum existing inside the container actively sucks in the liquid that is filtered by the microfilter chosen. Compounding is followed by injection of enough air to suppress residual vacuum. Extraction of liquids from compartment 3 through tube 17 is similar to that discussed above. Replacement air is admitted through neck 252D.

The industrial preparation of containers shown in FIGS. 8 and 9 follows the patterns mentioned earlier.

In the embodiments discussed above, the filter has been shown in the container. However, as long as no contaminated material enters the container the purposes of the invention are realized. To that end, the filter could be moved into operative space 122 in FIGS. 8 and 9 so that air or other materials entering tubes 117 or 260 would be filtered prior to the entry therethrough.

From what was described heretofore with respect to the various modes of embodiment of the invention, it appears that the containers can be kept free from any undesired particle, particularly during extemporaneous utilization and compounding in a contaminated environment.

The invention is not limited to the embodiments described. On the contrary, more variations may be conceived within the realm of the invention.

I claim:

1. In a container for allowing selected addition to and removal from the contents thereof, a first compartment in the container having a first opening to the outside of the container, and means for closing the first opening, a second compartment in the container, having a second opening to the outside of the container, the first and second compartments being separated by a filter for preventing contaminants in the first compartment from entering the second compartment, the improvement comprising:

seal means in the second opening for sealing the second opening, tube means through the seal means for communicating with the second compartment, first stopper means for sealing the tube means, means for mounting the seal means at the second opening to create an operative space on the outside of the seal means, second stopper means on the side of the operative space opposite the seal means for sealing the second opening and for preventing contamination to the operative space, whereby removal of the second stopper means gives access to the operative space and to the first stopper and the tube means.

2. The improvement of claim 1 wherein the first compartment is within the second compartment, the filter comprising a cartridge-filter, and the first compartment being bounded by the cartridge filter.

3. The improvement of claim 2 further including mounting means on the seal means for mounting the filter in the second opening.

4. The improvement of claim 3 wherein the second opening is a neck extending from the surface of the container the seal means being mounted in the neck and supporting the tube means to extend through the neck, the seal means having the support means for supporting the filter from the seal means.

5. The improvement of claim 4 wherein the seal means comprises a lower seal means and means for supporting the lower seal means in the neck and an upper seal means on the lower seal means, lip means on the tube means for holding the tube means between the upper seal means and the lower seal means, the lip means having support means for supporting a portion of the filter whereby the portion of the filter is held between the upper and lower seal means.

6. The improvement of claim 5 wherein the upper seal means comprises a membrane of pierceable material whereby the membrane may be pierced above the filter for adding material to the first compartment so that it can be filtered into the second compartment for ultimate removal through the tube means.

7. The improvement of claim 6 wherein the second stopper means includes locating means for being positioned over the filter whereby access to the filter and the first compartment may be made by piercing through the second stopper and the upper seal means.

8. The improvement of claim 7 further comprising cap means and means on the neck for securing the cap means to the neck, the cap means covering the second stopper means to secure the second stopper to the upper seal means.

9. The improvement of claim 8 wherein the cap means has a removable portion, and means for aligning the removable portion above the locating means whereby the removable portion can be removed to permit access to the locating means to allow the second stopper and the upper seal means to be pierced without removing all of the cap means.

10. The improvement of claim 1 wherein the tube means includes an opening at the top thereof and the first stopper means comprises a lid for covering the opening for preventing the contaminants from entering the tube to flow into the second compartment, the second stopper having means thereon for holding the lid in sealing engagement with the tube means when the second stopper means is urged toward the seal means.

11. The improvement of claim 10 further comprising valve means on the tube means for selectively opening and closing the tube means, the second stopper means further comprising valve closing means for engaging the valve means for closing it when the second stopper means is urged toward the seal means.

12. The improvement of claim 1 wherein the filter comprises filtering elements adapted to filter different sized particles plurality of passage means connecting each of the filtering elements with the outside of the container through the first opening, and valve means for directing material from the outside of the container to a selected one of the passage means and for selectively blocking access from the outside of the container to the other passage means.

13. The improvement of claim 12 wherein the second opening includes an upper and a lower ledge, the seal means being mounted between the upper and lower ledges and resilient means mounted between the upper and lower ledges for urging the seal means against the second opening to seal the second opening.

14. The improvement of claim 1 wherein the seal means comprises an upper seal means and a lower seal means, means on the tube means for being secured, between the upper and lower seal means in the second opening.

15. The improvement of claim 1 including means for removably mounting the second stopper means in the second opening.

16. The improvement of claim 1 comprising a filter opening through the seal means spaced apart from tube means and a filter in the opening extending from the operative space to the inside of the container for filtering materials to be added to the container through the filter opening.

17. The improvement of claim 16 wherein the second stopper means comprises a penetrable membrane over at least a portion thereof, the membrane being located above the filter whereby the second stopper does not have to be removed to provide access to the filter for adding material to the container.

18. The improvement of claim 1 further comprising a neck for forming the second opening, and cap means fixed to the neck for holding the second stopper means in the second opening, the cap means having a removable portion aligned with the membrane of the second stopper means over the filter means.

19. The improvement of claim 1 wherein the seal means is in the second opening, and the operative space is in the second opening.

20. A method of preparing a container for dispensing fluid through an opening, the opening having a seal and a tube extending through the seal, the method comprising:

placing a lid on the portion of the tube extending outside of the seal so that air in the container can pass out of the tube by lifting the lid slightly, exposing the container to high vacuum whereby air in the container is removed therefrom, exposing the container to air pressure whereby the pressure forces the lid into the tube to seal the tube to prevent contaminants from passing through the seal and the tube into the container, mounting a stopper over the seal with a space between the seal and the stopper prior to exposing the container to the vacuum whereby air escaping from the container through the tube can pass beyond the stopper and whereby after removal of air from the container and exposing the container to pressure, the pressure differential between the outside of the container and the space between the seal and the stopper forces the stopper into the opening to seal the opening, and providing the stopper with means for engaging the lid whereby downward movement of the stopper into the opening also assists in pushing the lid into the tube.

21. The method of claim 20 wherein a valve is mounted on the tube for allowing passage of fluid through the tube when the valve is open and blocking the tube when the valve is closed, the method further comprising closing the valve with a portion of the stopper when air pressure forces the stopper into the opening.

22. A hermetically sealed evacuated container for dispensing liquids and adapted to receive liquid additives without exposing the liquids to be dispensed to outside contaminants which comprises a container having an opening to the outside, a closure for said opening including an upper removable seal and a lower fixed seal spaced from the upper removable seal and cooperating therewith in defining an operative space compartment sealed from both the interior of the container and the outside, said lower seal having an inlet passageway and an outlet passageway therethrough joining the interior of the container with said operative space compartment, independent seal means for each passageway accessible from said operative space compartment, a porous solid filter having a myriad of pores for separating contaminants from liquid additives or air entering the inside of said container, said inlet passageway being constructed and arranged to communicate with said solid filter for stopping ingress of contaminants into the container when the passageway is functional to accommodate flow into the container, a valve in said outlet passageway upstream from said independent seal for said outlet passageway, mounting means accommodating removal of said upper seal to open said operative space compartment to the outside giving access to said independent inlet and outlet passageway seals, and said independent seal for said inlet passageway being openable when said upper seal is removed to permit controlled vacuum induced introduction of liquid additives and air into the container and said independent seal for said outlet passageway being removable and said valve being openable for outflow of liquids from the container with said introduction of liquid additives and air passing through the filter before entering the container.

23. The container of claim 22 wherein the outlet passageway projects into the operative space compartment for mating with tubing to dispense the contents of the container.

24. A sealed container adapted to receive and dispense fluids without contamination which comprises, a bottle having a neck, a seal assembly fitted to said neck and sealed twice therewith at two spaced levels, said seal assembly including a lower seal fixed to said neck and a removable upper seal spaced from said lower seal and cooperating therewith to define therebetween at said neck an operative space compartment sealed from both the inside and outside of said bottle, said lower seal having an inlet passageway and an outlet passageway protruding on both sides thereof joining the interior of said bottle with said operative space compartment, independent seal means for each passageway accessible from said operative space compartment, said upper seal being removable from outside said bottle to give access to said independent seal means, a solid filter having a myriad of pores associated with said inlet passageway to filter fluid before it enters the bottle, said portion of the outlet passageway projecting into said operative space compartment constructed and arranged to mate with tubing for dispensing the contents of the bottle, said portion of the inlet passageway projecting into said operative space compartment constructed and arranged to receive means to insert additives into the bottle, the independent seal means being selectively openable to permit flow of fluid therethrough whereby any fluid entering the bottle through the inlet passageway is filtered before it can be dispensed from the outlet passageway, and a valve in said outlet passageway upstream from said independent seal means for said outlet passageway.

25. The seal assembly of claim 24 including a tip end on each passageway projecting into said operative space compartment receiving the independent seal means, and said upper seal closing the mouth of the neck of the bottle and overlying said tip ends of the passageways to protect said ends against contamination.

26. A hermetically sealed evacuated container for dispensing liquids and adapted to receive liquid additives without exposing the liquids to be dispensed to outside contaminants which comprises a container having an opening to the outside, a closure for said opening including an upper removable seal and a lower fixed seal spaced from the upper removable seal and cooperating therewith in defining an operative space compartment sealed from both the interior of the container and the outside, said lower seal having an inlet passageway and an outlet passageway therethrough joining the interior of the container with said operative space compartment, an independent seal means for said inlet passageway accessible from said operative space compartment, a porous solid filter having a myriad of pores for separating contaminants from liquid additives of air entering the inside of said container, said inlet passageway being constructed and arranged to communicate with said solid filter for stopping ingress of contaminants into the container when the passageway is functional to accommodate flow into the container, a valve in said outlet passageway accessible from said operative space compartment controlling outflow through said outlet passageway, mounting means accommodating removal of said upper seal to open said operative space compartment to the outside giving access to said independent seal means for said inlet passageway and said valve in said outlet passageway, said independent seal for said inlet passageway being operable when said upper seal is removed to permit controlled vacuum induced introduction of liquid additives and air into the container, and said valve in said outlet passageway being openable for outflow of liquids from the container with said introduction of liquid additives and air passing through the filter before entering the container.

27. A sealed container for dispensing liquids without exposing the liquids to be dispensed to outside contaminants which comprises a container having an opening to the outside, a closure for said opening including an upper removable seal and a lower fixed seal spaced from the upper removable seal and cooperating therewith in defining an operative space compartment sealed from both the interior of the container and the outside, said lower seal having an inlet passageway and an outlet passageway therethrough joining the interior of the container with said operative space compartment, an independent seal means for said inlet passageway accessible from said operative space compartment, a porous solid filter having a myriad of pores for separating contaminants from liquid additives or air entering the inside of said container, said inlet passageway being constructed and arranged to communicate with said solid filter for stopping ingress of contaminants into the container when the passageway if functional to accommodate flow into the container, a valve in said outlet passageway accessible from said operative space compartment controlling outflow through said outlet passageway, mounting means accommodating removal of said upper seal to open said operative space compartment to the outside giving access to said independent seal means for said inlet passageway and said valve in said outlet passageway, said independent seal for said inlet passageway being openable when said upper seal is removed to permit introduction of air into the container, and said valve in said outlet passageway being openable for outflow of liquids from the container with said introduction of air passing through the filter before entering the container.

* * * * *